United States Patent [19]
Shimmick et al.

[11] Patent Number: 5,549,597
[45] Date of Patent: Aug. 27, 1996

[54] IN SITU ASTIGMATISM AXIS ALIGNMENT

[75] Inventors: John K. Shimmick, Belmont; Charles R. Munnerlyn, Sunnyvale, both of Calif.

[73] Assignee: Visx Incorporated, Santa Clara, Calif.

[21] Appl. No.: 308,480

[22] Filed: Sep. 19, 1994

Related U.S. Application Data

[63] Continuation of Ser. No. 58,733, May 7, 1993, abandoned.

[51] Int. Cl.$^6$ .................................................. A61B 17/36
[52] U.S. Cl. ................................................ 606/5; 606/10
[58] Field of Search ................................. 606/4, 5, 6, 10, 606/11, 12, 14; 351/208, 211, 212, 246

[56] References Cited

U.S. PATENT DOCUMENTS

| | | | |
|---|---|---|---|
| 3,084,694 | 4/1963 | Kavanagh et al. | 606/4 |
| 4,298,253 | 11/1981 | Tagnon | 351/246 |
| 4,409,979 | 10/1983 | Roussel et al. | 606/4 |
| 4,861,154 | 4/1989 | Sherwin et al. | 351/211 |

Primary Examiner—Angela D. Sykes
Assistant Examiner—Sonya Harris-Ogugua
Attorney, Agent, or Firm—Graham & James LLP

[57] ABSTRACT

An alignment module for determining the astigmatic axis of a patient and for aligning the cylindrical axis of a laser ablation system for ophthalmological surgery. A rotatable image element, such as target, is illuminated through a diffuser plate and an image of the target is presented along an optical path comprising a fixed collimating lens, a plurality of turning mirrors and a slidably adjustable imaging lens. The light source, diffuser plate, lenses and mirrors are all mounted on a platform which is attachable to a camera port of a surgical microscope normally installed in the delivery system optics of the laser surgery system. The movable lens is adjusted to a position corresponding to the required sphere correction, and the target is rotated until the patient sees the clearest target image, signifying alignment of the target with the astigmatic axis of the patient's eye. The alignment angle information is used to align the cylinder axis of the laser surgery system to the proper angle.

22 Claims, 6 Drawing Sheets

IN SITU ASTIGMATISM AXIS ALIGNMENT

This is a continuation of application Ser. No. 08/058,733, filed May 7, 1993, now abandoned.

BACKGROUND OF THE INVENTION

This invention relates to ophthalmological surgery techniques for providing refractive corrections to the eye of a patient. More particularly, this invention relates to a method and apparatus for determining the astigmatism axis of a patient's eye in association with a surgical procedure.

Ophthalmological surgery techniques are known for correcting the refractive characteristics of a patient's eye to improve vision. One such technique is radial keratotomy, a surgical procedure which involves altering the contour of the cornea by making radial incisions through the corneal surface in a preselected peripherally distributed pattern. Another such technique known as photorefractive keratectomy (PRK) employs an ultraviolet laser to generate a beam capable of producing ablative photodecomposition of corneal tissue, the irradiated flux density and exposure time of the cornea to the ultraviolet laser radiation being so controlled as to provide a surface sculpting of the cornea to achieve a desired ultimate surface change in the cornea. Ultraviolet laser based systems and methods are disclosed in the following U.S. patents and patent applications, the disclosures of which are hereby incorporated by reference: U.S. Pat. No. 4,665,913 issued May 19, 1987 for "METHOD FOR OPHTHALMOLOGICAL SURGERY"; U.S. Pat. No. 4,669,466 issued Jun. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. patent application Ser. No. 109,812 filed Oct. 16, 1987 for "LASER SURGERY METHOD AND APPARATUS"; and U.S. Pat. No. 5,163,934 issued Nov. 17, 1992 for "PHOTOREFRACTIVE KERATECTOMY".

In the above-cited U.S. Pat. No. 4,665,913 several different techniques are described which are designed to effect corrections for specific types of optical errors in the eye. For example, a myopic condition, is corrected by laser sculpting the corneal surface to flatten the curvature. In addition, an astigmatic condition, which is typically caused by a cylindrical component of curvature departing from the otherwise generally spherical curvature of the surface of the cornea, is corrected by effecting cylindrical ablation about the axis of cylindrical curvature of the eye. Other optical errors can be corrected in a similar fashion.

Prior to performing a surgical procedure to effect a refractive correction for astigmatism, it is essential to determine the astigmatic axis of the patient's eye. A patient having astigmatism with spherical correction along one refractive meridian will see point sources of images smeared along a line. Consequently, a line which is aligned with the smear in an astigmatic eye's image will still appear as a line, but will become blurred when it is rotated. Patterns such as radial lines have been used in the past to approximately locate a patient's refractive cylinder axis. Another technique for making such a determination is disclosed in U.S. Pat. No. 3,785,723 issued Jan. 15, 1974 for "METHOD AND APPARATUS FOR LOCATING A PRINCIPLE MERIDIAN OF AN ASTIGMATIC OPTICAL SYSTEM", the disclosure of which is hereby incorporated by reference. In the '723 patent, a prior art technique is described, which employs a rotatable target in the form of an opaque disk with a series of small apertures arranged in a straight line along one diameter of the disk and illuminated from behind by a light source, thereby causing each of the apertures to appear as a point source of light. An imaging lens system having variable dioptric power is placed before the patient's eye for the purpose of correcting the refractive error of the eye or for aiding in the process of correcting the refractive error. If the eye is astigmatic, the image of each point aperture will appear to the patient as an image line segment. If the line drawn through the small apertures is aligned along the astigmatic axis (termed the "principle meridian" in the '723 patent), the image of the apertures will appear to the patient as a series of short line segments mutually aligned along a common axis. If the target is not so aligned with respect to the astigmatic axis of the patient's eye, the image will appear as a series of short line segments aligned in a mutually parallel fashion but laterally displaced from one another. By rotating the target until the short line segments are mutually aligned, the astigmatic axis can be determined with reference to a set of orthogonal reference coordinates. This information can then be used to align the laser apparatus to perform the cylindrical correction along the proper cylindrical axis. The '723 patent also discloses several embodiments of an improvement over the basic technique using a rotatable target, the improvements generally relating to various optical arrangements mechanically linked to the rotatable target for rotation therewith to provide better line segment image generation. It should be noted that the '723 patent teaches that the test image may be focused and aligned by the patient, by an examiner using auxiliary optical means to view the retina of the patient's eye, or by an auxiliary optical system having appropriate photoelectric detection means. Also, this patent states that the accuracy of the technique can be improved by using monochromatic or near-monochromatic light to form the test image.

While the '723 technique has been found useful for locating the astigmatic axis of a patient's eye, it does not provide in situ astigmatic axis alignment information just prior to ophthalmological surgery. In situ astigmatic axis alignment information for purposes of this invention is defined as such alignment information while the patient is in position for the corrective surgical technique and, more specifically, just prior to the start of the surgery. In situ astigmatic axis alignment is highly desirable since it provides real time information for adjustment of the cylinder axis of the laser surgery system and eliminates possible sources of alignment errors, such as rotation of the eye in the socket when the patient's horizontal reference is removed (e.g., when the patient is lying in a supine position in the operating chair) and rotation of the eye in the socket due to a shift from binocular to monocular viewing (e.g., when the patient views a target image with one eye through a monocular viewing instrument).

SUMMARY OF THE INVENTION

The invention comprises a method and apparatus for providing in situ astigmatic axis alignment which eliminates potential sources of alignment error and provides real time alignment information while the patient is in position for a surgical procedure.

From an apparatus standpoint, the invention comprises an alignment system for enabling in situ determination of the astigmatic axis of an eye. The system includes means for providing a target image viewable by an eye, the means preferably including a source of radiation, a target having an image pattern and a diffuser plate positioned between the source and the target to project the image downstream of the target. The pattern image preferably comprises three sets of three lines with different line spacings corresponding to vision of 20/20, 20/25, and 20/30. Alternatively, multiple apertures of the type described above may be used for the image pattern. A collimating lens positioned downstream of the target directs the image along a light path, which is preferably folded by means of mirrors, prisms or the like, in order to provide a compact light path.

The system further includes means for enabling the image to be translated along an image path to a position corresponding to a desired sphere correction value. The enabling means preferably includes a base, a guide mounted on the base for providing the translation path, and an imaging lens slidably mounted on the guide and manipulatable by the patient or an attending technician or physician. An indicator coupled to the imaging lens is associated to a scale bearing sphere correction information to facilitate determination that the target has achieved the appropriate vergence (as seen by the patient).

Means for enabling the image to be rotated about an axis to a position corresponding to the astigmatic axis of the eye is also provided, this means including a base, a target bearing the target pattern rotatably mounted on the base, and a manually operable device, such as a knob, coupled to the target. The knob is provided with an indicator, such as a pointer, and a scale bearing angular position information is associated to the indicator to provide a ready determination of the angular position of the astigmatic axis.

From a method standpoint, the invention includes the steps of presenting a target image viewable by an eye, translating the target image along an image path until the image reaches a position corresponding to a desired sphere correction value, rotating the image about an axis while viewing the image until the target as seen by the patient achieves the desired end point, and determining the angular position of the image referenced to a zero point. For a target image in the shape of a bar pattern, the desired endpoint is sharpness of the finest bar pattern which can be seen by the patient. In the case of the multiple apertures, the desired endpoint is alignment of the line segments.

From a different method aspect, the invention includes the steps of arranging a patient in a preoperative position, presenting an image corresponding to a desired sphere correction value for the patient's eye to a position viewable by the patient, rotating an image element about an axis while the patient views the image until the image achieves a desired end point, and determining the angular position of the image referenced to a predetermined coordinate location. The step of presenting an image includes the step of translating the image along a path, preferably by translating an imaging lens along a translation path, until the image reaches a position corresponding to the desired sphere correction value. The step of rotating may alternately include the step of rotating the image about an axis or rotating an optical component, such as a cylindrical lens, about the axis.

When used in association with a laser surgical device for performing ophthalmological surgery, the astigmatic axis alignment system is mounted to the camera port of a surgical microscope containing optical elements providing the remainder of the image path, typically a beam deflection element, such as a mirror or prism, and an objective lens. To facilitate in situ alignment, the imaging lens position and angular position of the target can be preset to the approximate prescription of the patient so that a reasonably distinct image is presented to the patient prior to adjusting the system.

The invention provides a simple and reliable technique for enabling the patient or an attending physician or technician to quickly and precisely determine the angular position of the astigmatic axis referenced to a predetermined zero reference point while the patient is in situ just prior to commencement of the opthomological surgical procedure. Once this information has been obtained, it is transferred to the laser surgery system to ensure that the astigmatic laser correction is performed along the proper cylinder axis. The invention can be conveniently incorporated into existing laser surgery systems by retrofitting the optical and mechanical elements, or may be designed into future systems. Also, the lens translation and image element rotating mechanisms may be automated and controlled by a suitable computer.

For a fuller understanding of the nature and advantages of the invention, reference should be had to the ensuing detailed description, taken in conjunction with the accompanying drawings.

BRIEF DESCRIPTION OF THE DRAWINGS

FIG. 9 is a top edge view of the FIG. 6 device; and.

DESCRIPTION OF THE PREFERRED EMBODIMENT

Figure 1:
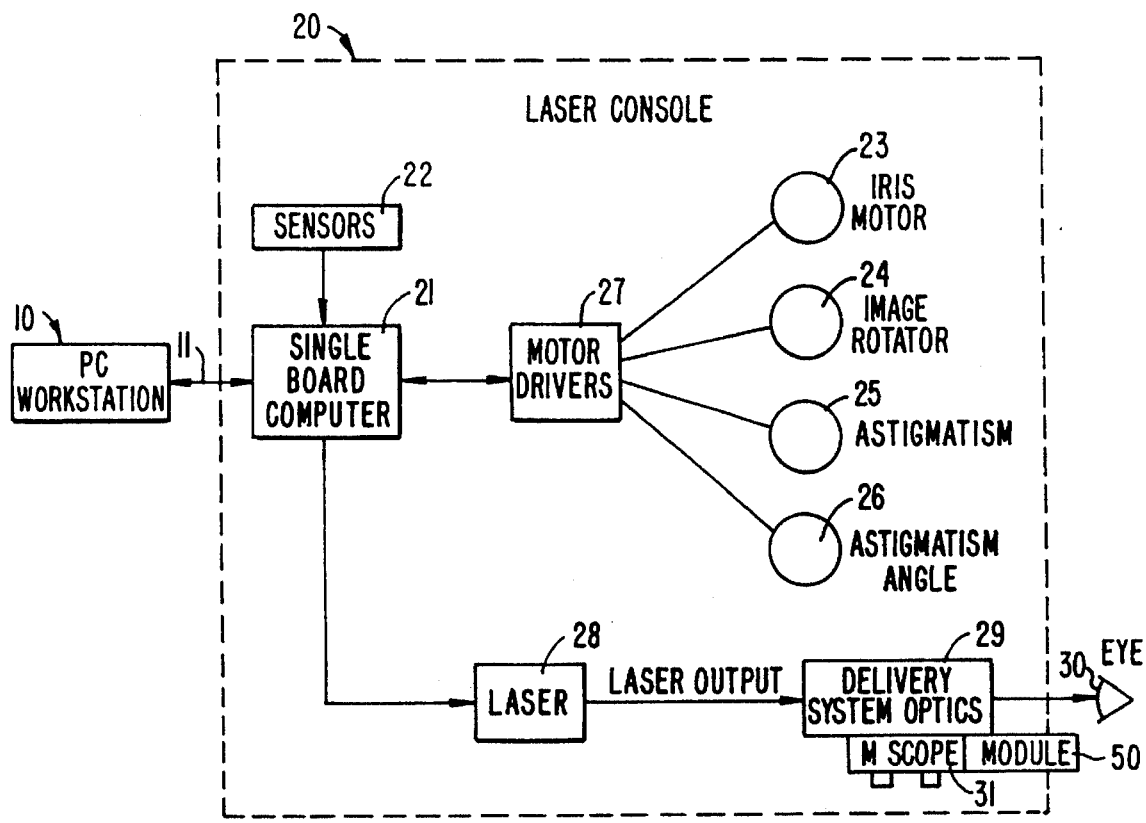
FIG. 1 is a block diagram of a laser surgery system incorporating the invention.

Turning now to the drawings, FIG. 1 illustrates a block diagram of an ophthalmological surgery system incorporating the invention. As seen in this Fig., a personal computer (PC) work station 10 is coupled to a single board computer 21 of a laser surgery unit 20 by means of a first bus connection 11. PC work station 10 and the subcomponents of laser surgery unit 20 are known components and preferably comprise the elements of the VISX TWENTY/ TWENTY EXCIMER LASER SYSTEM available from Visx, Incorporated of Sunnyvale, Calif. Thus, the laser surgery system 20 includes a plurality of sensors generally designated with reference numeral 22 which produce feedback signals from the movable mechanical and optical components in the laser optical system, such as the elements driven by an iris motor 23, an image rotator 24, an astigmatism motor 25 and an astigmatism angle motor 26. The feedback signals from sensors 22 are provided via appropriate signal conductors to the single board computer 21, which is preferably an STD bus compatible single board computer using a type 8031 microprocessor. The single board computer 21 controls the operation of the motor drivers generally designated with reference numeral 27 for operating the elements 23–26. In addition, single board computer 21 controls the operation of the Excimer laser 28, which is preferably an argon-fluorine laser with a 193 nanometer wavelength output designed to provide feedback stabilized fluence of 160 joules per $cm^2$ at the cornea at the patient's eye 30 via the delivery system optics generally designated with reference numeral 29. A surgical microscope 31, preferably an operating microscope available from Möller Wedel of Hamburg, Germany, is attached to the delivery system optics 29 to afford physician viewing of the eye 30 to enable positioning of the eye 30 in the ablation plane prior to laser surgery. Other ancillary components of the laser surgery system 20 which are not necessary to an understanding of the invention, such as a video monitor for the microscope, a patient eye retention system, and an ablation effluent evacuator/filter, as well as the gas delivery system, have been omitted to avoid prolixity. Similarly, the keyboard, display, and conventional PC subsystem components (e.g., flexible and hard disk drives, memory boards and the like) have been omitted from the depiction of the PC work station 10.

Figure 2:
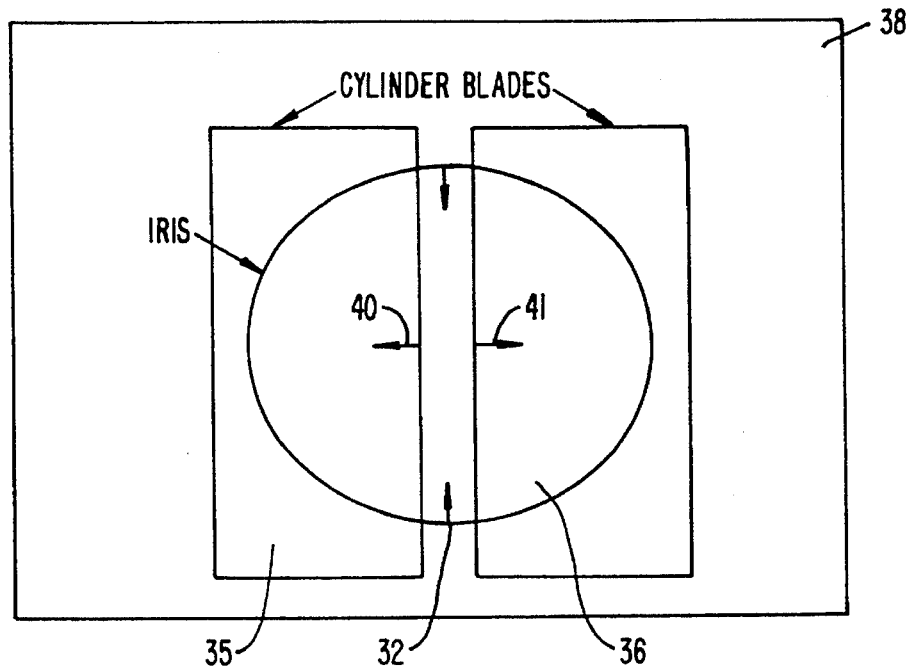
FIG. 2 is a schematic front view showing the elements of the laser surgery system which provide cylindrical correction to the eye.

The iris motor 23 is used to control the diameter of a variable diameter iris schematically depicted in FIG. 2. The astigmatism motor 25 is used to control the separation distance between a pair of cylinder blades 35, 36 which are mounted on a platform 38 for bi-directional translatory motion in the direction of arrows 40, 41. Platform 38 is rotatably mounted on a second platform (not illustrated) and is rotationally driven by astigmatism angle motor 26 in a conventional way in order to enable alignment of the slit axis (illustrated in a vertical orientation in FIG. 2) with the cylinder axis of the patient's eye. Iris 32 is driven by iris motor 23 in a known way to change the diameter of the iris opening from a fully opened position (the position illustrated in FIG. 2) to a fully closed position in which the aperture is closed to a minimum diameter of 0.8 mm. It is understood that the variable diameter iris 32 and the cylinder blades 35, 36 are positioned with respect to the output of laser 28 in such a manner as to intercept the beam prior to irradiation of the corneal surface of the patient's eye 30. For the purpose of this application, it may be assumed that iris 32 and cylinder blades 35, 36 are part of the delivery system optics subunit 29 shown in FIG. 1.

Figure 3:
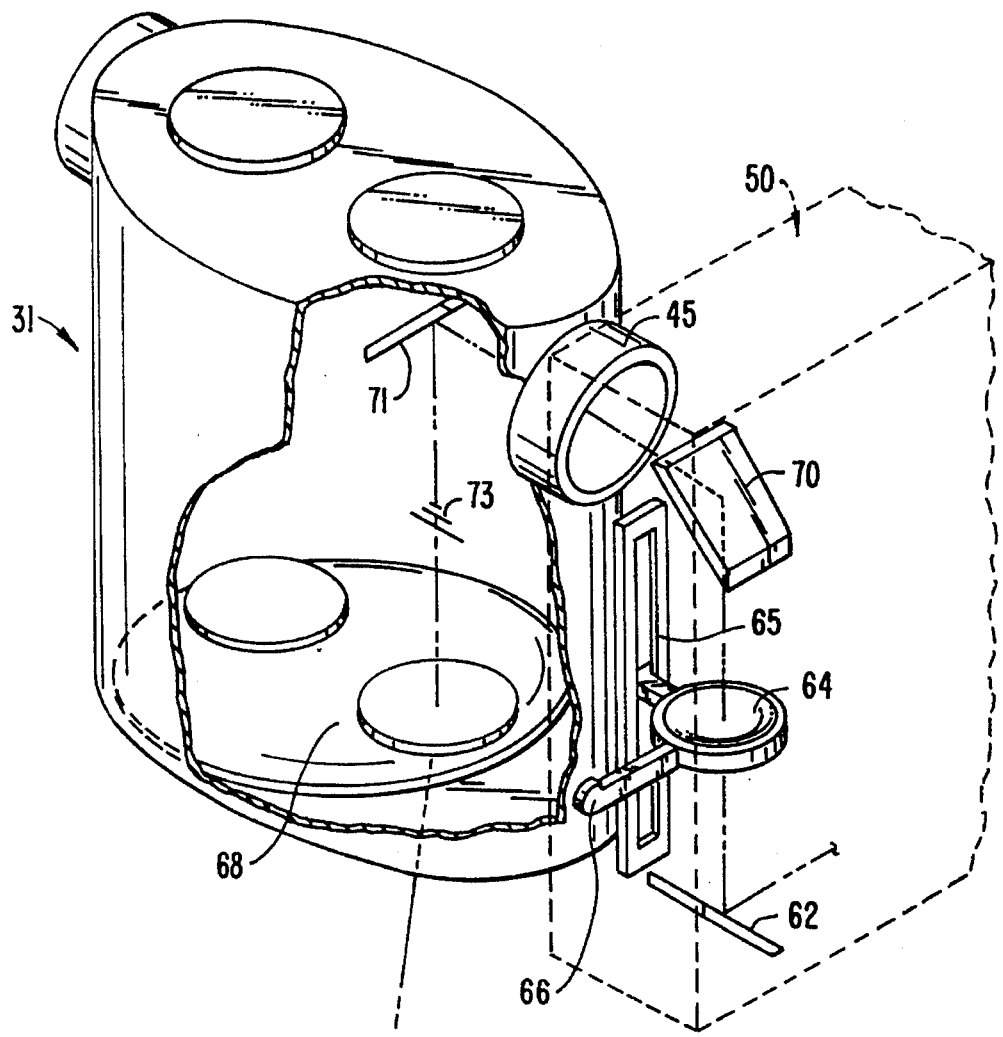
FIG. 3 is a schematic view of the preferred embodiment of the invention mounted on a surgical microscope.
Figure 5:
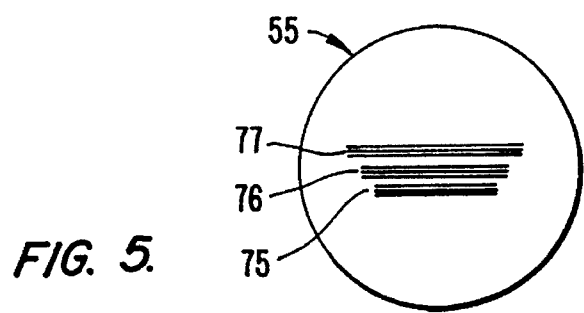
FIG. 5 is a plan view of the preferred target.
Figure 4:
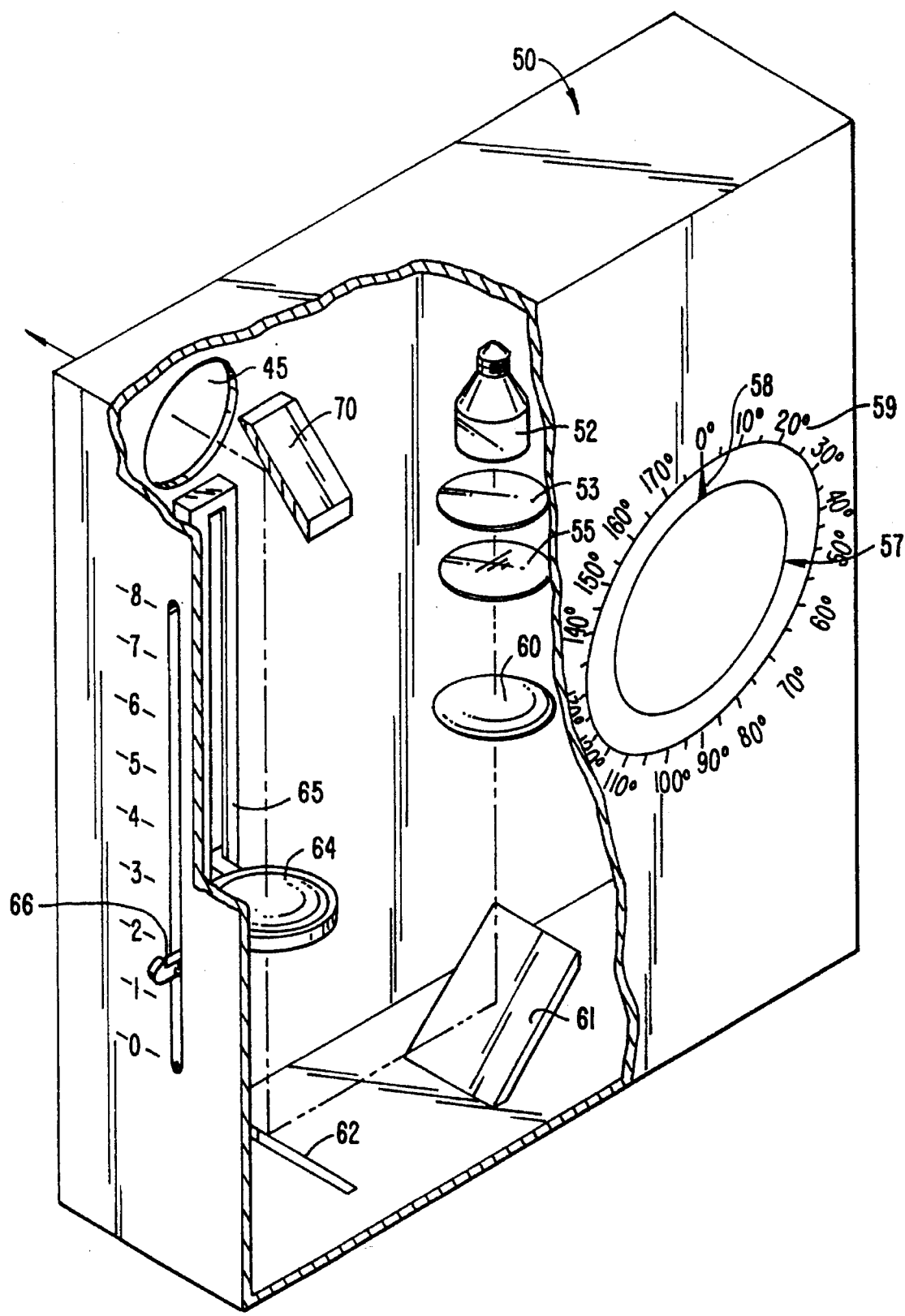
FIG. 4 is a schematic front view of the preferred embodiment of the invention with the cover partially broken away to show the optical elements.
Figure 6:
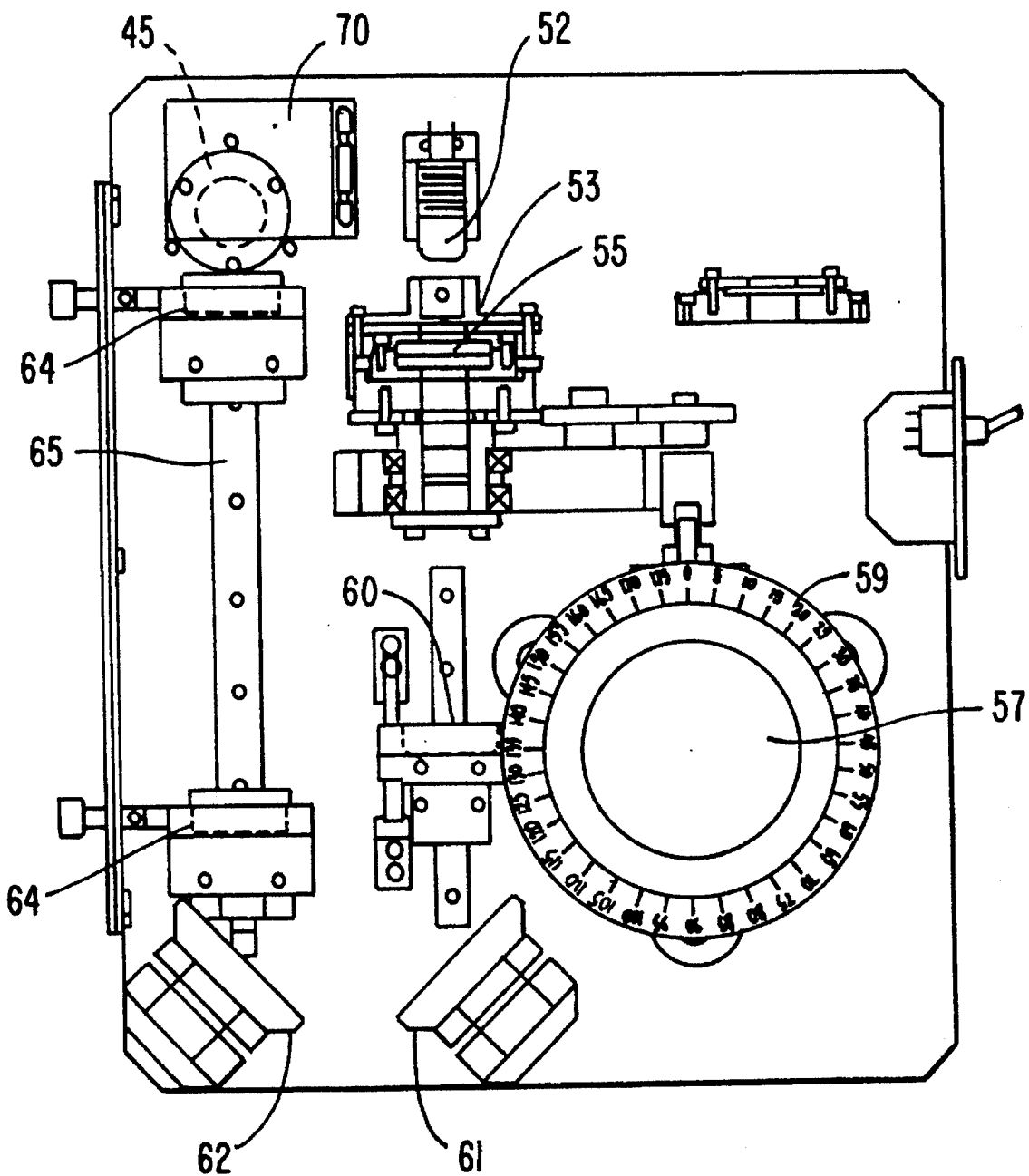
FIG. 6 is a front view of the actual embodiment with the cover removed.
Figure 7:
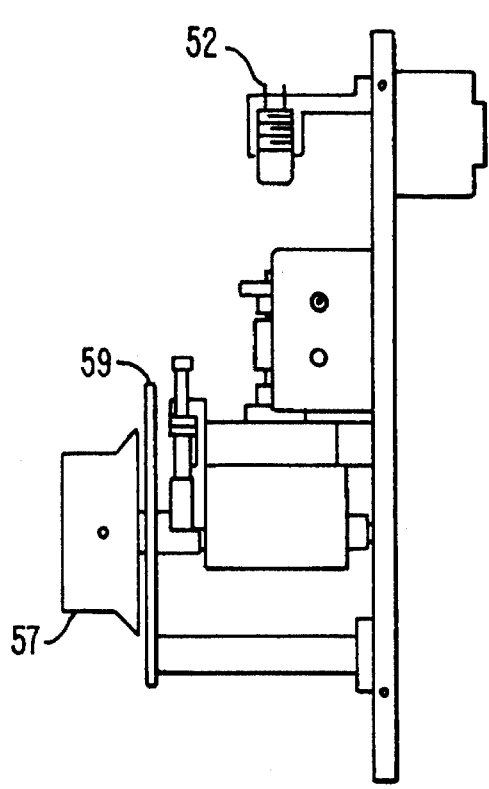
FIG. 7 is a right edge view of the FIG. 6 device.
Figure 8:
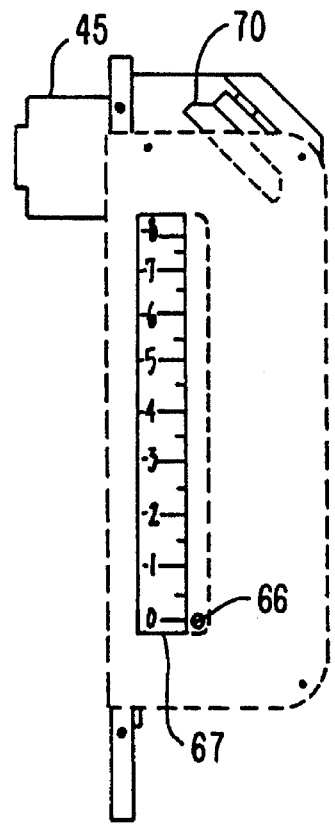
FIG. 8 is a left edge view of the FIG. 6 device.
Figure 9:
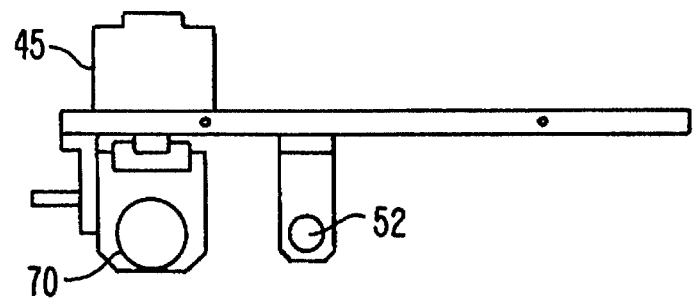
Figure 10:
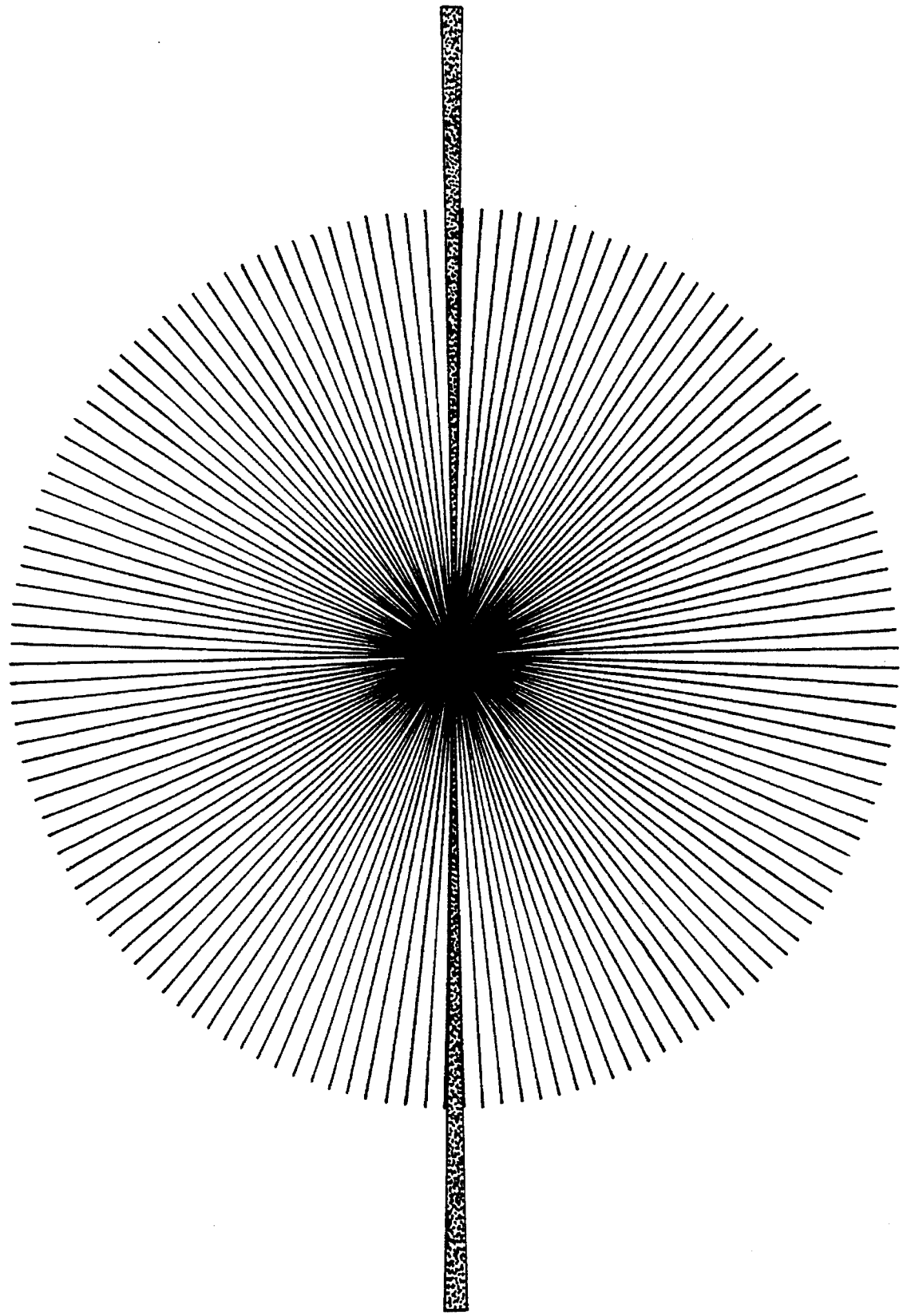
FIG. 10 is a plan view of a wedge target.

In order to provide in situ alignment of the cylinder axis of the laser system 20 with the astigmatic axis of the patient's eye, an astigmatic axis alignment module is provided for system 20. FIGS. 3 and 4 illustrate the alignment module in schematic form. With reference to these Figs., a module generally designated with reference numeral 50 is designed to be attached to one of the camera ports 45 of the surgical microscope 31. Module 50 includes an image light source 52, preferably a tungsten filament light bulb of appropriate intensity (e.g., 5 watts) or an LED of appropriate wavelength and intensity, and a diffuser plate 53 for diffusing the light radiation emitted by source 52. If desired, more than one bulb may be used. A suitable target 55, such as the target shown in FIG. 5 or FIG. 10, is rotatably mounted below the diffuser plate to provide a target image to be viewed by the patient. Target 55 is mechanically linked to a rotatable knob 57 having a pointer 58, and a scale 59 is provided which denotes angular amounts at appropriate angles.

A first lens 60, which is preferably a 100 mm focal length achromatic lens, is provided in the light path below the rotatable target 55 and functions to substantially collimate the light from the target 55. A pair of mirrors 61, 62 redirect the light upwardly through a second lens 64 which is slidably mounted on a rail 65 so as to be vertically adjustable by means of a manually operable lever 66. Lens 64, which is preferably a 250 mm focal length achromatic lens, functions to form an image near the back focal length of the objective lens 68 of the surgical microscope 31. For this purpose, a third mirror 70, is provided in the alignment module 50, and a beam splitter 71, which is already present in the surgical microscope 31, is used to direct the image 73 to the eye 30.

The position of the image of the target 55 relative to the cornea as seen by the patient can be varied by sliding lens 64 along rail 65 using lever 66. Various positions of lens 64 along the rail 65 correspond to different spherical corrections for the patient's refraction. The corresponding spherical correction for each position is labelled on the outside of the module as a scale 67 calibrated in diopters as shown in FIG. 4. Sliding lens 64 along rail 65 changes the position of the image 73 formed by lens 64 relative to the back focal length of the microscope objective 68. For myopic patients, the virtual image is closer to the patient's cornea, and for emmetropic patients, the virtual image is infinitely far from the patient's cornea. Because the light entering lens 64 is collimated, the image formed by lens 64 is of constant size as lens 64 is displaced along rail 65. Consequently, the size of the target 55 as seen by the patient is nearly constant.

The module 50 is physically positioned so that the patient can manipulate knob 57 and view the image 73 while resting in the operating chair in the proper position for the surgical procedure. In use, with the patient in the proper position, lens 64 is adjusted to correct for the patient's sphere and the knob 57 is adjusted to the approximate astigmatic axis of the patient, using previously obtained patient refractive information. This permits the patient to at least crudely see the image 73 of target 55. Thereafter, the patient rotates the knob 57 until the desired end point is obtained. When the FIG. 5 target is used, the desired endpoint is reached when the patient sees the finest bar pattern most clearly. When the spaced multiple apertures target is used, the desired endpoint is reached when the lines corresponding to the apertures are aligned. The patient is preferably permitted to repeat this procedure several times so that the average angular value indicated by pointer 58 and scale 59 can be noted and entered into the computer 10. It should be noted that, if the patient does not wish to perform the adjustments of lens 64 and knob 57, an assisting technician or the physician may perform the adjustment while the patient guides the operator by oral feedback.

With reference to FIG. 5, the preferred target 55 comprises three sets 75–77 of three lines. The line spacing is varied and corresponds to vision of 20/20, 20/25 and 20/30, respectively. The patient is instructed to rotate target 55 until the finest set of lines can be seen with maximum clarity. This target provides greater accuracy than one containing merely a single set of coarse lines or a single row of dots. However, if desired, other targets may be employed.

An important aspect of the invention lies in the ease with which target 55 can be aligned relative to the ablation cylinder axis of system 20. To perform this alignment, the cylinder axis of system 20 is set to a value of 90°, a plastic target is located in the normal position of eye 30 during surgery, and a 0.5 to 1.0 mm by 6.0 mm slit is ablated into the plastic. Diffuser plate 53 and lens 64 are removed, target 55 is inserted and the pattern is projected onto the ablated slit in the plastic. During this projection, lens 60 colimates the light from target 55 and microscope objective 68 brings the image from target 55 into focus near the plane of the ablation. Next, the operator views the registration of the image on the ablation slit through the microscope 31 and rotates knob 57 until the target image is exactly parallel with the ablation slit. Knob 57 is then loosened and repositioned to the zero degree position. The alignment process is now complete.

The actual construction of the module 50 is illustrated in FIGS. 6–9. The same reference numerals are used in these Figs. to identify elements corresponding to those shown in FIGS. 3 and 4.

FIG. 10 illustrates an alternate target comprising a set of radial lines equally distributed about the center of the target, and a pair of oppositely disposed facing wedge-shaped portions. The target is used by rotating while viewing until the lines straddling the wedge-shaped portions appear as clear as the patient's vision permits.

In order to properly position the patient before determination of the astigmatic axis, the depth of field on the microscope 31 is used. This can position the patient to within a few millimeters of the desired position. In addition, the entrance pupil of the patient's eye is centered in an eyepiece reticule (not illustrated) in microscope 31. Alternatively, the reticule may comprise a projection reticule from a heads up display.

As will now be apparent, the invention provides a simple and convenient technique for determining the astigmatic axis of a patient's eye in situ and for aligning the cylinder axis of the laser ablation apparatus with this axis. While the precision of the alignment depends to some extent on the subjective reaction of the patient, actual results to within a residual cylinder error of ¼ Diopter have been achieved in actual practice. Further, involving the patient in the alignment process can add a psychological benefit to the entire surgical experience, which is highly desirable. In addition, the invention can be conveniently attached to the laser surgery system without the need for extensive redesign.

Although the preferred embodiment has been described with reference to manually adjustable lens and target positions, an automated version of the system is contemplated as well. In such a system, the p.c. workstation 10 can be coupled to additional motor drivers and position encoders operatively coupled to lens 64 and the platform for target 55 to automatically translate and rotate these elements in response to the actuation of push button switches or the equivalent by the patient. In such a system, the sphere correction and cylindrical axis angular position information received by the computer 10 is then used to control the ablation procedure to achieve the desired sculpting of the anterior corneal surface. Further, automatic initial presetting may be incorporated into the system so that lens 64 and target 55 are prepositioned to the approximate positions by entering the patient's refractive information into computer 10 and initiating an automatic presetting routine. The system may be further refined by incorporating a topographical mapping capacity to optically measure the surface contours of the cornea and feed this information to the computer 10 to establish the treatment parameters.

While the preferred embodiment has been described with reference to a rotatable target 55, other variations using different rotatable image elements are envisioned. For example, a stationary target may be provided along with a cylindrical lens with appropriate power, the cylindrical lens being mounted in a holder rotatable about the optical axis—either by means of knob 57 or appropriate motor driven elements. In such an alternate embodiment, lens 64 is first adjusted for the proper sphere correction, after which the cylindrical lens is rotated until the patient perceives the clearest image or otherwise achieves the desired end point. If desired, lens 64 may be replaced with a spherocylindrical lens to combine the sphere correction and cylindrical axis location optics into a single lens element. In such an embodiment, the lens mechanism is modified to provide rotational motion as well as the translatory motion afforded by rail 65 and lever 66. This may be done by linking the lens holder to the knob 57 or by providing a modified lens rotation mechanism and angular scale closer to the lens location. In a still further variation, both a cylindrical lens and a Jackson cross can be positioned along the optical path—preferably adjacent lens 64. In this variation, the Jackson cross can be used to determine the location of the patient's cylindrical axis by manipulating the device in the normal fashion, and the cylindrical lens and Jackson cross can be rotated until the desired end point is achieved. In another variation, a cylindrical lens and Jackson cross can be located below the microscope objective 68 and rotatably mounted in a suitable holder with an angular position scale or encoder.

While the above provides a full and complete disclosure of the preferred embodiment of the invention, various modifications, alternate constructions and equivalents may be employed as desired. For example, other line spacings corresponding to different vision than those listed above for target 55 may be used, and other targets than the preferred target illustrated in FIG. 5 can also be used, such as the targets illustrated in the above referenced '723 patent or other known prior art targets. In addition, the astigmatic axis alignment information can be automatically provided to the computer 10 by attaching a conventional angular encoder to knob 57 or target 55. Once the patient has adjusted knob 57 to the optimum position, the patient or an attending technician or physician may then signal the computer by depressing a push button switch. After repeated measurements, the computer then calculates the average value and automatically selects the optimum astigmatism angle by operating the appropriate motor drivers 27. In addition, the system can be modified to provide motor driven motion to lens 64 and the target platform so that the adjustments can be made by activating push button switches or the equivalent. Therefore, the above description should not be construed as limiting the scope of the invention, which is defined by the appended claims.

What is claimed is:

1. A laser surgery system having a laser beam generating means laser beam delivery optical elements for directing a laser beam along a beam path to a plane of ablation substantially normal to said beam path, and an alignment system for enabling in situ determination of an astigmatic axis of an eye of a patient when in an operative position at said plane of ablation, said alignment system including:

means for providing a target image viewable by the eye of a patient when in said operative position at said plane of ablation of said laser surgery system, said target image providing means including a target having an image pattern and a light collimating lens positioned downstream of said target;

first means for enabling said image to be translated along an image path to a position corresponding to a desired sphere correction value, said first means including a moveable imaging lens positioned downstream of said collimating lens; and second means for enabling said image to be rotated about an axis to a position corresponding to the astigmatic axis of the eye.

2. The invention of claim 1 wherein said means for providing a target image includes a source of radiation and a diffuser plate positioned between said source and said target.

3. The invention of claim 1 wherein said means for providing a target image includes light path folding means for providing a compact light path.

4. The invention of claim 1 wherein said first enabling means includes a base and a guide mounted on said base for providing a translation path; and wherein said imaging lens is slidably mounted on said guide.

5. The invention of claim 4 further including an indicator moveable with said imaging lens and a scale bearing sphere correction information.

6. The invention of claim 1 wherein said second means for enabling said image to be rotated includes a base; wherein said target is rotatably mounted on said base; and wherein said second means further includes manually actuatable means coupled to said target.

7. The invention of claim 6 wherein said manually actuatable means includes a knob.

8. The invention of claim 6 further including indicator means coupled to said manually actuatable means and a scale bearing angular position information.

9. The invention of claim 6 further including an encoder coupled to said base for generating angular position information, and computer means coupled to said encoder for receiving and processing said angular position information.

10. A method for enabling in situ determination of an astigmatic axis of an eye of a patient, the eye having an anterior corneal surface with a portion thereof located adjacent an intended plane of ablation of a laser surgery system having laser beam delivery optical elements for directing a laser beam along a beam path to the plane of ablation, the plane of ablation being substantially normal to the laser beam path, said method comprising the steps of:

(a) presenting a target image viewable by the eye of said patient in an operative position at the plane of ablation of the laser surgery system, said step of providing including the steps of irradiating a target having an image pattern and collimating the target image;

(b) translating said target image along a path until the image reaches a position corresponding to a desired sphere correction value;

(c) rotating said image about an axis of rotation having an angular reference position while viewing the image until the patient's perspective of the image achieves a desired endpoint; and (d) determining the angular axial position of the image with reference to said angular reference position.

11. The invention of claim 10 wherein said step (a) of presenting includes the step of irradiating a target bearing an image through a light diffuser plate.

12. The method of claim 10 wherein said step (b) of translating includes the step of translating an imaging lens along a translation path.

13. The method of claim 10 wherein said step (c) of rotating includes the step of rotating a target bearing said target image about an axis.

14. The method of claim 10 wherein said step (d) of determining includes the step of noting the angular position of a pointer coupled to a target bearing said target image.

15. The method of claim 10 wherein the target image comprises a line target image, and wherein the desired endpoint comprises an image of greatest clarity.

16. A method for enabling in situ determination of an astigmatic axis of a patient's eye, the eye having an anterior corneal surface with a portion thereof located adjacent an intended plane of ablation of a laser surgery system having laser beam delivery optical elements for directing a laser beam along a beam path to the plane of ablation, the plane of ablation being substantially normal to the laser beam path, said method comprising the steps of:

(a) arranging the patient in a preoperative position with the patient's eye at the plane of ablation of the laser surgery system;

(b) presenting an image corresponding to a desired sphere correction value for the eye to a position viewable by the patient by irradiating an image element having an image pattern and collimating the resulting image;

(c) rotating the image element about an axis of rotation having an angular reference position while the patient views the image until the patient's perception of the image achieves a desired end point; and (d) determining the angular axial position of the image element with reference to said angular reference position.

17. The method of claim 16 wherein said step (b) of presenting includes the step of translating the image along a path until the image reaches a position corresponding to the desired sphere correction value.

18. The method of claim 17 wherein said step of translating includes the step of translating an imaging lens along a translation path.

19. The method of claim 16 wherein said step (c) of rotating includes the step of rotating the image about an axis.

20. The method of claim 16 wherein the image element comprises an imaging device.

21. The method of claim 20 wherein said imaging device comprises a cylindrical lens mounted for rotation about said axis; and wherein said step of rotating includes the step of rotating the cylindrical lens about said axis.

22. The invention of claim 1 wherein said target image providing means further includes a microscope having a beam splitter positioned along said image path downstream of said first enabling means.

* * * * *